United States Patent [19]

Fischer et al.

[11] 4,001,217
[45] Jan. 4, 1977

[54] AZETIDINYL CARBOTHIOLATES

[75] Inventors: Adolf Fischer, Mutterstadt;
Hanspeter Hansen, Ludwigshafen;
Wolfgang Rohr, Mannheim, all of Germany

[73] Assignee: BASF Aktiengesellschaft,
Ludwigshafen (Rhine), Germany

[22] Filed: Nov. 5, 1975

[21] Appl. No.: 629,064

Related U.S. Application Data

[63] Continuation of Ser. No. 446,674, Feb. 28, 1974, abandoned.

[30] Foreign Application Priority Data

Mar. 10, 1973 Germany .......................... 2312045

[52] U.S. Cl. ................................. 260/239 A; 71/88
[51] Int. Cl.² ...................................... C07D 205/04
[58] Field of Search ................... 260/239 A, 326.4; 71/100

[56] References Cited

UNITED STATES PATENTS 3,066,020  11/1962  Tilles et al. ..................... 260/326.4

FOREIGN PATENTS OR APPLICATIONS 284,666  4/1965  Australia ............................ 71/100

*Primary Examiner*—Donald G. Daus
*Assistant Examiner*—Mark L. Berch
*Attorney, Agent, or Firm*—Johnston, Keil, Thompson & Shurtleff

[57] ABSTRACT

New and valuable carbothiolates of azetidines having a good herbicidal action, herbicides containing these compounds, and a process for controlling the growth of unwanted plants with these compounds.

1 Claim, No Drawings

AZETIDINYL CARBOTHIOLATES

This is a continuation of application Ser. No. 446,674 filed Feb. 28, 1974, now abandoned.

The present invention relates to new and valuable carbothiolates of azetidines having a good herbicidal action, herbicides containing these compounds, and a process for controlling the growth of unwanted plants with these compounds.

It is known from German Patent 1,300,947 to use S-ethyl-hexahydro-1H-azepine-1-carbothiolate for controlling unwanted plants in crops such as barley, wheat and rice. However, its action is poor.

We have now found that carbothiolates of azetidines of the formula

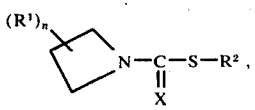

where $R^1$ denotes alkyl (methyl, ethyl), n denotes one of the integers 0, 1, 2, 3 and 4, X denotes oxygen or sulfur, and $R^2$ denotes an aliphatic radical (methyl, ethyl, propyl, isopropyl, butyl, sec-butyl, tert-butyl, allyl, propargyl, butynyl, isobutynyl, β-hydroxyethyl, β-chloroethyl, dichloroallyl, trichloroallyl, 2-methyl-3-dichloroallyl, β-cyanoethyl, β-methoxyalkyl) which may be substituted one or more times by halogen, hydroxyl, cyano or alkoxy, or $R^2$ denotes the radical of the formula

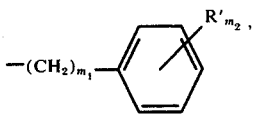

where R' denotes halogen (fluoro, chloro, bromo, iodo), nitro, cyano, alkoxy (methoxy, ethoxy) or alkyl (methyl, ethyl), $m_1$ denotes one of the integers 0, 1 and 2 and $m_2$ denotes one of the integers 0, 1, 2, 3 and 4 and, if $m_2$ is greater than 1, the substituents for R' may be identical or different, have a good herbicidal action. The compounds of the invention have the same herbicidal action as, and often a better action than, S-ethyl-hexyhydro-1H-azepine-1-carbothiolate, combined with superior crop plant compatibility.

The active ingredients may be prepared by reacting a thiol chloroformate with an optionally substituted azetidine. The compounds may also be prepared by allowing azetidines in the form of the appropriate N-acyl chlorides to react with mercaptans.

The preparation of the azetidines is well known from the literature.

EXAMPLE 1

S-ethyl-(2,2,4-trimethylazetidine)-1-carbothiolate

At 30° to 40° C, 6.23 parts (by weight) of thioethyl chloroformate is dripped into a mixture of 4.95 parts of 2,2,4-trimethylazetidine and 6 parts of triethylamine in 50 parts of benzene.

After 1 hour the triethylamine hydrochloride is separated by suction filtration and the filtrate is washed with water. After drying, concentration is carried out in vacuo and the residue distilled off.

There is obtained 6.70 parts of S-ethyl(2,2,4-trimethyl-azetidine)-1-carbothiolate of the formula:

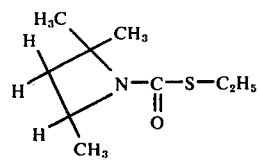

Boiling point (0.1 mm Hg): 59° C.

The following compounds may be prepared by the same process:

S-methyl-(2,2,4-trimethylazetidine)-1-carbothiolate, b.p. (0.05 mm): 70° C

S-propyl(2,2,4-trimethylazetidine)-1-carbothiolate, b.p. (0.05 mm): 81° C s-isopropyl-(2,2,4-trimethylazetidine)-1-carbothiolate, b.p. (0.01 mm): 67° to 71° C S-sec-butyl-(2,2,4-trimethylazetidine)-1-carbothiolate, b.p. (0.01 mm): 75° to 80° C S-trichloroallyl-(2,2,4-trimethylazetidine)-1-carbothiolate, b.p. (0.01 mm): 130° C S-benzyl-(2,2,4-trimethylazetidine)-1-carbothiolate, b.p. (0.01 mm): 135° C S-(p-chlorobenzyl)-(2,2,4-trimethylazetidine)-1-carbothiolate, b.p. (0.05 mm): 154° C S-benzyl-(3,3-dimethylazetidine)-1-carbothiolate, b.p. (0.01 mm): 128° C S-(β-phenylethyl)-(2,2,4-trimethylazetidine)-1-carbothiolate, b.p. (0.01 mm): 120° to 125° C, $n_{20}$: 1.5398

S-(β-phenylethyl)-(3,3-dimethylazetidine)-1-carbothiolate, b.p. (0.01 mm): 140° to 145° C, $n_{20}$: 1.5996

S-benzyl-(2,2,4-trimethylazetidine)-1-thiolcarbothiolate, b.p. (0.01 mm): 160° C, $n_{25}$: 1.6026

S-propyl-(2,2,4-trimethylazetidine)-1-thiolcarbothiolate, b.p. (0.01 mm): 100° C, $n_{25}$: 1.5540

S-benzylazetidine-1-carbothiolate,

S-ethylazetidine-1-carbothiolate,

S-propylazetidine-1-carbothiolate,

S-isopropylazetidine-1-carbothiolate,

S-benzyl-(2-methylazetidine)-1-carbothiolate,

S-butyl-(2,2,4-trimethylazetidine)-1-carbothiolate, b.p. (0.01 mm): 90° to 95° C, $n_{20}$: 1.4835.

Application may be effected for instance in the form of directly sprayable solutions, powders, suspensions, dispersions, emulsions, oil dispersions, pastes, dusts, or granules by spraying, atomizing, dusting, broadcasting or watering. The form of application depends entirely on the purpose for which the agents are being used; in any case it should ensure a fine distribution of the active ingredient.

For the preparation of solutions, emulsions, pastes and oil dispersions to be sprayed direct, mineral oil fractions of medium to high boiling point, such as kerosene or diesel oil, further coal-tar oils and oils of vegetable or mineral origin, aliphatic, cyclic or aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalene-sulfonic acids, phenolsulfonic acids, alkylaryl sulfonates, alkyl sulfates, and alkyl sulfonates, alkali metal and alkaline earth metal salts of dibutyl-naphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silica gel, silicic acid, silicates, talc, kaolin, Attaclay, limestone, lime, chalk, bole, loecs, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90% by weig of active ingredient.

There may be added to the compositions or individual active ingredients (if desired, immediately before use) oils of various types, herbicides, fungicides, nematocides, insecticides, bactericides, trace elements, fertilizers, antifoams (e.g., silicones), growth regulators, antidotes and other herbicidally effective compounds such as substituted anilines, substituted aryloxycarboxylic acids and salts, esters and amides thereof, substituted ethers, substituted arsonic acids and their salts, esters and amides, substituted benzimidazoles, substituted benzo sothiazoles, substituted benzothiadiazinone dioxides, substituted benzoxazines, substituted benzoxazinones, substituted benzothiadiazoles, substituted biurets, substituted quinolines, substituted carbamates, substituted aliphatic carboxylic acids and their salts, esters and amides, substituted aromatic carboxylic acids and their salts, esters and amides, substituted carbamoylalkylthiol or -dithiophosphates, substituted quinazolines, substituted cycloalkylamidocarbothiolic acids and their salts, esters and amides, substituted cycloalkylcarbonamidothiazoles, substituted dicarboxylic acids and their salts, esters and amides, substituted dihydrobenzofuranyl sulfonates, substituted disulfides, substituted dipyridylium salts, substituted dithiocarbamates, substituted dithiophosphoric acids and their salts, esters and amides, substituted ureas, substituted hexahydro-1H-carbothioates, substituted hydantoins, substituted hydrazides, substituted hydrazonium salts, substituted isooxazole pyrimidones, substituted imidazoles, substituted isothiazole pyrimidones, substituted ketones, substituted naphthoquinones, substituted aliphatic nitriles, substituted aromatic nitriles, substituted oxadiazoles, substituted oxadiazinones, substituted oxadiazolidine diones, substituted oxadiazine diones, substituted phenols and their salts and esters, substituted phosphonic acids and their salts, esters and amides, substituted phosphonium chlorides, substituted phosphonalkylglyzines, substituted phosphites, substituted phosphoric acids and their salts, esters and amides, substituted piperidines, substituted pyrazoles, substituted pyrazole alkylcarboxylic acids and their salts, esters and amides, substituted pyrazolium salts, substituted pyrazolium alkyl sulfates, substituted pyridazines, substituted pyridazones, substituted pyridine carboxylic acids and their salts, esters and amides, substituted pyridines, substituted pyridine carboxylates, substituted pyridinones, substituted pyrimidines, substituted pyrimidones, substituted pyrrolidine carboxylic acid and its salts, esters and amides, substituted pyrrolidines, substituted pyrrolidones, substituted arylsulfonic acids and their salts, esters and amides, substituted styrenes, substituted tetrahydrooxadiazine diones, substituted tetrahydrooxadiazole diones, substituted tetrahydromethanoindendes, substituted tetrahydrooxadiazole thiones, substituted tetrahydrothiadiazine thiones, substituted tetrahydrothiadiazole diones, substituted aromatic thiocarbonylamides, substituted aromatic thiocarbonylamides, substituted thiocarboxylic acids and their salts, esters and amides, substituted thiol carbamates, substituted thioureas, substituted thiophosphoric acids and their salts, esters and amides, substituted triazines, substituted triazoles, substituted uracils, and substituted uretidine diones. The last-mentioned herbicidal compounds may also be applied before or after the active ingredients or compositions thereof according to the invention.

These agents may be added to the herbicides according to the invention in a ratio by weight of from 1 : 10 to 10 : 1. The same applies to oils, fungicides, nematocides, insecticides, bactericides, antidotes and growth regulators.

The agents according to the invention may be applied either once or several times before or after planting, before sowing, pre- or postemergence, or during emergence of the crop plants or weeds.

The amount applied may vary and depends in essence on the effect to be achieved. Rates are generally from 0.1 to 15 kg and more, preferably from 0.2 to 6 kg per hectare.

The new active ingredients have a strong herbicidal action and may be used as weedkillers or for controlling the growth of unwanted plants. Whether the new active ingredients are used as total or selective agents depends in essence on the amount of ingredient used per unit area.

By "weeds" and "unwanted plant growth" we mean all monocotyledonous and dicotyledonous plants which grow in loci where they are not desired. The agents according to the invention may therefore be used for controlling for instance Gramineae, such as Gramineae, such as
    Cynodon spp.                         Dactylis spp.
    Digitaria spp.                      Avena spp.
    Echinochloa spp.               Bromus spp.
    Setaria spp.                          Uniola spp.
    Panicum spp.                       Poa spp.
    Alopecurus spp.                Leptochloa spp.
    Lolium spp.                         Brachiaria spp.
    Sorghum spp.                     Eleusine spp.
    Agropyron spp.                 Cenchrus spp.
    Phalaris spp.                      Eragrostis spp.
    Apera spp.                          etc.;
Cyperaceae, such as
    Carex spp.
    Cyperus spp.                     Eleocharis spp.
    Scirpus spp.                         etc.;
dicotyledonous weeds, such as
Malvaceae, e.g.
    Abutilon theoprasti         Hibiscus spp.
    Sida spp.                           etc.;
    Malva spp.
Compositae, such as
    Ambrosia spp.                  Centaurea spp.
    Lactuca spp.                     Tussilago spp.
    Senecia spp.                      Lapsana communis
    Sonchus spp.                     Tagetes spp.
    Xanthium spp.                  Erigeron spp.
    Iva Spp.                           Anthemis spp.
    Galinsoga spp.                 Matricaria spp.
    Taraxacum spp.                Artemisia spp.
    Chrysanthemum spp.        etc.;
    Bidens spp.
    Cirisum spp.
Convolvulaceae, such as
    Convolvulus spp.              Cuscuta spp.
    Ipomoea spp.                     etc.;
    Jaquemontia tamnifolia
Cruciferae, such as
    Barbarea vulgaris            Arabidopsis thaliana
    Brassica spp.                    Descurainia spp.
    Capsella spp.                    Draba spp.
    Sisymbrium spp.               Coronopus didymus
    Thlaspi spp.                     Lepidium spp.
    Sinapis arvensis              etc.;
    Raphanus spp.
Geraniaceae, such as
    Erodium spp.                     etc.;
    Geranium spp.
Portulacaceae, such as
    Portulaca spp.                 etc.;
Primulaceae, such as
    Anagallis arvensis           etc.;
    Lysimachia spp.
Rubiaceae, such as
    Richardia spp.                 Diodia spp.
    Galium spp.                      etc.;
Scrophulariaceae, such as
    Linaria spp.                     Digitalis spp.
    Veronica spp.                    etc.;
Solanaceae, such as
    Physalis spp.                    Nicandra spp.
    Solanum spp.                     etc.;
    Datura spp.
Urticaceae, such as
    Urtica spp.                        etc.;
Violaceae, such as
    Viola spp.                          etc.;
Zygophyllaceae, such as
    Tribulus terrestis             etc.;
Euphorbiaceae, such as
    Mercurialis annua            Euphorbia spp.
Umbelliferae, such as
    Daucus carota                 Ammi majus
    Aethusa cynapium            etc.;
Commelinaceae, such as
    Commelina spp.                etc.;
Labiatae, such as
    Lamium spp.                     etc.;
    Galeopsis spp.
Leguminosae, such as
    Medicago spp.                 Sesbania exaltata
    Trifolium spp.                  Cassia spp.
    Vicia spp.                         etc.;
    Lathyrus spp.
Plantaginaceae, such as
    Plantago spp.                   etc.;
Polygonaceae, such as
    Polygonum spp.                Fagopyrum spp.
    Rumex spp.                        etc.;
Aizoaceae, such as
    Mollugo verticillata          etc.;
Amaranthaceae, such as
    Amaranthus spp.               etc.;
Boraginaceae, such as
    Amsinckia spp.                 Anchusa spp.
    Myostis spp.                     etc.;
    Lithospermum spp.
Caryophyllaceae, such as
    Stellaria spp.                  Silene spp.
    Spergula spp.                  Cerastium spp.
    Saponaria spp.                 Agrostemma githago
    Scleranthus annuus          etc.;
Chenopodiaceae, such as
    Chenopodium spp.             Atriplex spp.
    Kochia spp.                       Monolepsis nuttaliana
    Salsola kali                      etc.;
Lythraceae, such as
    Cuphea spp.                     etc.;
Oxalidaceae, such as
    Oxalis spp.                        etc.;
Ranunculaceae, such as
    Ranunculus spp.               Adonis spp.
    Delphinium spp.               etc.;
Papaveraceae, such as
    Papaver spp.                    etc.;
    Fumaria officinalis
Onagraceae, such as
    Jussiaea spp.                    etc.;
Rosaceae, such as
    Alchemillia spp.                etc.;
    Potentilla spp.
Potamogetonaceae, such as
    Potamogeton spp.             etc.;
Najadaceae, such as
    Najas spp.                         etc.;
Marsileaceae, such as
    Marsilea quadrifolia         etc.

The new agents may be employed in cereal crops, such as
    Avena spp.                         Sorghum
    Triticum spp.                   Zea mays
    Hordeum spp.                  Panicum miliaceum
    Secale spp.                       Oryza spp.
and in dicotyledon crops, such as
Cruciferae, e.g.
    Brassica spp.                  Raphanus spp.
    Sinapis spp.                    Lepidium spp.
Compositae, e.g.
    Lactuca spp.                   Carthamus spp.
    Helianthus spp.               Scorzonera spp.
Malvaceae, e.g.
    Gossypium hirsutum
Leguminosae, e.g.
    Medicago spp.                 Phaseolus spp.
    Trifolium spp.                  Arachis spp.
    Pisum spp.                       Glycine max.
Chenopodiaceae, e.g.
    Beta vulgaris
    Spinacia spp.
Solanaceae, e.g.
    Solanum spp.                   Capsicum annuum
    Nicotiania spp.
Linaceae, e.g.
    Linum spp.
Umbelliferae, e.g.
    Petroselinum spp.            Apium graveolens
    Daucus carota
Rosaceae, e.g.
    Fragaria
Cucurbitaceae, e.g.
    Cucumis spp.                   Cucurbita spp.
Liliaceae, e.g.
    Allium spp.
Vitaceae, e.g.
    Vitis finifera
Bromeliaceae, e.g.
    Ananas sativus.

EXAMPLE 2

In the greenhouse loamy sandy soil was filled into pots and sown with various seeds. The soil prepared in this manner was then immediately treated with 1 kg per hectare of active ingredients I, II, IV, V, VI and VII and, for comparison, with 1 kg per hectare prior art compound III, each compound being emulsified or dispersed in 500 liters of water per hectare.

During the experiment the plants were provided with large amounts of water. After 4 weeks it was ascertained that active ingredients I, II, IV, V, VI and VII had better crop plant compatibility and a better herbicidal action than comparative compound III.

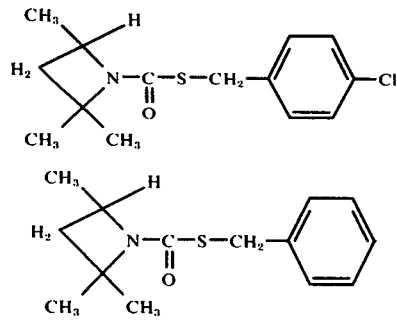

I

II

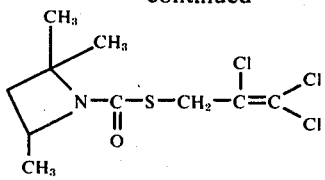

VI

-continued

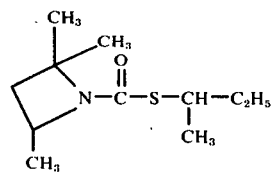

VII

The results of this experiment are given below.

| Active ingredient kg/ha | I 1 | II 1 | III 1 | IV 1 | V 1 | VI 1 | VII 1 |
|---|---|---|---|---|---|---|---|
| Crop plants: | | | | | | | |
| Brassica napus | 0 | 0 | 10 | 0 | 0 | 0 | 0 |
| Triticum aestivum | 0 | 0 | 5 | 0 | 0 | 0 | 0 |
| Unwanted plants: | | | | | | | |
| Echinochloa crus-galli | 100 | 90 | 40 | 95 | 90 | 60 | 80 |
| Lolium multiflorum | 100 | 100 | 20 | 100 | 95 | 80 | 85 |
| Lolium perenne | 100 | 100 | 20 | 95 | 90 | 80 | 90 |
| Avena fatua | 60 | 80 | 0 | 60 | 55 | 40 | 70 |
| Poa annua | 100 | 100 | 30 | 100 | 85 | 85 | 100 |
| Poa trivialis | 100 | 100 | 30 | 95 | 85 | 85 | 95 |

0 = no damage
100 = complete destruction.

III

IV

V

EXAMPLE 3

Various plants were treated at a growth height of from 3 to 15 cm with 1 kg per hectare of each of the active ingredients I, II, IV, V, VI and VII and, for comparison, with 1 kg per hectare of comparative compound III, each compound being dispersed or emulsified in 500 liters of water per hectare.

During the experiment the plants were provided with large amounts of water. After 4 weeks it was ascertained that active ingredients I, II, IV, V, VI and VII had better crop plant compatibility than prior art agent III, combined with the same good herbicidal action.

| Active ingredient kg/ha | I 1 | II 1 | III 1 | IV 1 | V 1 | VI 1 | VII 1 |
|---|---|---|---|---|---|---|---|
| Crop plants: | | | | | | | |
| Brassica napus | 0 | 0 | 10 | 0 | 0 | 0 | 0 |
| Triticum aestivum | 0 | 0 | 5 | 0 | 0 | 0 | 0 |
| Unwanted plants: | | | | | | | |
| Echinochloa crus-galli | 100 | 90 | 40 | 95 | 90 | 60 | 90 |
| Lolium multiflorum | 100 | 100 | 20 | 95 | 90 | 70 | 90 |
| Lolium perenne | 100 | 100 | 20 | 90 | 85 | 70 | 85 |
| Avena fatua | 60 | 80 | 0 | 50 | 45 | 40 | 50 |
| Poa annua | 100 | 100 | 30 | 95 | 90 | 70 | 90 |
| Poa trivialis | 100 | 100 | 30 | 90 | 90 | 65 | 85 |

0 = no damage
100 = complete destruction.

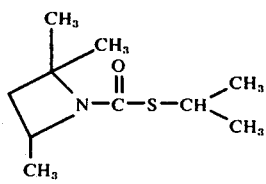

EXAMPLE 4

90 parts by weight of compound I is mixed with 10 parts by weight of N-methyl-α-pyrrolidone. A mixture is obtained which is suitable for application in the form of very fine drops.

EXAMPLE 5

20 parts by weight of compound II is dissolved in a mixture consisting of 80 parts by weight of xylene, 10 parts by weight of the adduct of 8 to 10 moles of ethylene oxide to 1 mole of oleic acid-N-monoethanolamide, 5 parts by weight of the calcium salt of dodecylbenzenesulfonic acid, and 5 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 6

20 parts by weight of compound I is dissolved in a mixture consisting of 40 parts by weight of cyclohexanone, 30 parts by weight of isobutanol, 20 parts by weight of the adduct of 7 moles of ethylene oxide to 1 mole of isooctylphenol, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 7

20 parts by weight of compound II is dissolved in a mixture consisting of 25 parts by weight of cyclohexanol, 65 parts by weight of a mineral oil fraction having a boiling point between 210° and 280° C, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 8

20 parts by weight of compound I is well mixed with 3 parts by weight of the sodium salt of diisobutylnaphthalene-$\alpha$-sulfonic acid, 17 parts by weight of the sodium salt of a ligninsulfonic acid obtained from a sulfite waste liquor, and 60 parts by weight of powdered silica gel, and triturated in a hammer mill. By uniformly distributing the mixture in 20,000 parts by weight of water, a spray liquid is obtained containing 0.1% by weight of the active ingredient.

EXAMPLE 9

3 parts by weight of compound II is intimately mixed with 97 parts by weight of particulate kaolin. A dust is obtained containing 3% by weight of the active ingredient.

EXAMPLE 10

30 parts by weight of compound I is intimately mixed with a mixture consisting of 92 parts by weight of powdered silica gel and 8 parts by weight of paraffin oil which has been sprayed onto the surface of this silica gel. A formulation of the active ingredient is obtained having good adherence.

We claim:
1. S-trichloroallyl-(2,2,4-trimethylazetidine)-1-carbothiolate.

* * * * *